(12) United States Patent
Borsotti et al.

(10) Patent No.: US 9,234,160 B2
(45) Date of Patent: Jan. 12, 2016

(54) PROCESS FOR THE PREPARATION OF COMPLEX OLIGOMERIC STRUCTURES

(71) Applicant: Novamont S.p.A., Novara (IT)

(72) Inventors: Giampietro Borsotti, Novara (IT); Francesca Digioia, Barengo (IT)

(73) Assignee: Novamont S.p.A., Novara (IL)

( * ) Notice: Subject to any disclaimer, the term of this patent is extended or adjusted under 35 U.S.C. 154(b) by 0 days.

(21) Appl. No.: 14/408,972

(22) PCT Filed: Jun. 18, 2013

(86) PCT No.: PCT/EP2013/062588
§ 371 (c)(1),
(2) Date: Dec. 18, 2014

(87) PCT Pub. No.: WO2013/189915
PCT Pub. Date: Dec. 27, 2013

(65) Prior Publication Data
US 2015/0152354 A1    Jun. 4, 2015

(30) Foreign Application Priority Data
Jun. 19, 2012 (IT) .............................. MI2012A1070

(51) Int. Cl.
| C11C 3/10 | (2006.01) |
| C07C 67/03 | (2006.01) |
| C11C 3/00 | (2006.01) |
| C11C 3/04 | (2006.01) |
| C07C 67/04 | (2006.01) |

(52) U.S. Cl.
CPC . *C11C 3/10* (2013.01); *C07C 67/03* (2013.01); *C11C 3/006* (2013.01); *C07C 67/04* (2013.01); *C11C 3/04* (2013.01)

(58) Field of Classification Search
None
See application file for complete search history.

(56) References Cited

U.S. PATENT DOCUMENTS

| 2009/0198004 A1* | 8/2009 | Brandenburger | ...... C08G 63/78 524/356 |
| 2009/0198005 A1* | 8/2009 | Brandenburger | ...... C08G 63/81 524/356 |
| 2011/0237812 A1 | 9/2011 | Benecke et al. | |
| 2011/0269979 A1 | 11/2011 | Benecke et al. | |
| 2012/0199515 A1* | 8/2012 | Peters | ................ B29C 47/0004 206/524.6 |

OTHER PUBLICATIONS

Abstract for JP2028147—Jan. 30, 1990 XP-002688980.

* cited by examiner

*Primary Examiner* — Yate K Cutliff
(74) *Attorney, Agent, or Firm* — Novak Druce Connolly Bove + Quigg LLP

(57) ABSTRACT

The invention relates to a process for the preparation of complex oligomeric structures obtained from vegetable oils. These structures comprise esters containing acid groups which are in turn esterified.

20 Claims, No Drawings

PROCESS FOR THE PREPARATION OF COMPLEX OLIGOMERIC STRUCTURES

CROSS REFERENCE TO RELATED APPLICATIONS

This application is a National Phase filing under 35 U.S.C. §371 of PCT/EP2013/062588 filed on Jun. 18, 2013; and this application claims priority to Application No. MI2012A001070 filed in Italy on Jun. 19, 2012 under 35 U.S.C. §119. The entire contents of each application are hereby incorporated by reference.

This invention relates to the process for the preparation of complex oligomeric structures obtained from vegetable oils, the said structures comprising esters containing acid groups which are in turn esterified.

These structures, characterised by high stability to hydrolysis and thermal oxidation, as well as having high viscosity, are used as a replacement for derivatives of materials of fossil origin and find application as extender oils and additives for rubbers, low pour point high stability lubricants, plasticisers for conventional plastics and bioplastics, polyurethane components, detergent components and bleaching agents, ink components, and monomeric units in thermoplastic and thermosetting polymers.

The prospect of increasingly more restricted availability of materials of fossil origin in nature such as petroleum now make it urgent to replace its derivatives with other compounds of natural origin. The requirement to use raw materials from renewable sources to ensure the eco-sustainability of industrial outputs is particularly apparent in the production of consumables, especially in the sectors of plastics, rubber and lubricants.

As far as the plastics industry is concerned, for example, bioplastics in which conventional monomers derived from oil are replaced by raw materials from renewable sources are being developed. With a view to increasing environmental sustainability it is necessary when replacing monomers to look towards increasingly more thorough conversion of present polymer formulations, including the additives used for their processing.

In the field of elastomers it is common practice to use extender oils having a plasticising action derived from the processing of oil to extend the volume of rubbers and thus reduce production costs. The use of these extender oils of mineral origin has disadvantages associated with the high toxicity and carcinogenicity of their components, such as polycyclic aromatic hydrocarbons (PAH).

Even as far as lubricants are concerned, there has long been an increasingly stringent need to replace mineral lubricants with lubricants of renewable origin.

One example of products of natural origin which do not have the disadvantages described above and are at the same time capable of providing functional properties which are substantially similar to those of conventional products of non-renewable origin are the complex oligomeric structures described in international patent application PCT/EP2011/073492.

These complex structures, of the ester type, are prepared from mixtures of triglycerides containing saturated dicarboxylic acids in the presence of monoalcohols through esterification reactions catalysed by strong acids. In particular the esterification reactions described in the abovementioned patent application are catalysed by sulfuric acid or sulfonic acids.

The process of preparing the said complex oligomer structures nevertheless requires that high temperatures be achieved. Under these temperature conditions, despite the fact that the water formed is removed from the reactor during the reaction, the use of sulfuric acid can give rise to appreciable corrosion problems in metal reactors.

Sulfonic acids, like paratoluenesulfonic acid or methanesulfonic acid, which can be used as alternatives to sulfuric acid, likewise give rise to corrosion problems. Furthermore, they can react with the short chain alcohols present in the reaction mixture, binding to these and forming sulfonic esters, which remove the catalyst from the reaction environment. Being volatile, these short chain esters, in particular esters of methanesulfonic acid, evaporate during separation of the excess alcohol and volatile esters, and constitute an impurity in this latter fraction.

It is therefore necessary to find a process for the synthesis of the said oligomeric structures which makes it possible to avoid these disadvantages.

In this respect it has surprisingly been found that performing the esterification reaction in the absence of catalyst or in the presence of acid catalysts consisting of one or more phosphorus compounds it is possible to avoid both the corrosion problems and the formation of impurities in the volatile fraction. Furthermore, surprisingly, the complex oligomeric structures prepared according to this invention have a glass transition temperature (Tg) which renders them particularly suitable as extender oils in elastomeric compositions as a replacement for oils of fossil origin.

In particular, one object of this invention is a process for the preparation of mixtures of triglyceride comprising one or more of the following oligomeric structures:

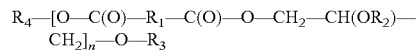

wherein $R_1$ is selected from $C_2$-$C_{22}$ alkylenes, $R_2$ is selected from one or more of the following groups consisting of $C_6$-$C_{24}$ dicarboxylic acid residues esterified with monoalcohols and $C_6$-$C_{24}$ monocarboxylic acid residues, $R_3$ is selected from one or more of the following groups consisting of H, $C_6$-$C_{24}$ dicarboxylic acid residues esterified with monoalcohols and $C_6$-$C_{24}$ monocarboxylic acid residues, $R_4$ is an alkyl group, n is an integer equal to or greater than 2, said $C_6$-$C_{24}$ dicarboxylic acids of $R_2$ and $R_3$ being esterified with monoalcohols and said mixture of triglycerides having a Number Average Molecular Weight (Mn) of between 800 and 10,000 Da, which comprises the step of esterification of a mixture of one or more triglycerides containing saturated dicarboxylic acids with alcohols at temperatures between 50 and 250° C. and which occurs in the absence of catalyst or in the presence of an acid catalyst consisting of one or more phosphorus compounds.

With reference to the structure above, $R_1$ is preferably a $C_6$-$C_{11}$ alkylene, $C_6$, $C_7$ and/or $C_{11}$ alkylenes being particularly preferred. The two or more $R_1$ in the structure may be different from each other.

$R_2$ represents $C_6$-$C_{24}$ dicarboxylic acid residues or $C_6$-$C_{24}$ monocarboxylic acid residues or a mixture thereof. The two or more $R_2$ in the structure may differ from each other.

$R_3$ represents $C_6$-$C_{24}$ dicarboxylic acid residues or $C_6$-$C_{24}$ monocarboxylic acid residues.

When $R_2$ and/or $R_3$ represent $C_6$-$C_{24}$ dicarboxylic acid residues the free acid groups in the $C_6$-$C_{24}$ dicarboxylic acid residues are esterified with straight or branched $C_1$-$C_{12}$ monoalcohols.

Short chain monoalcohols such as for example methyl alcohol, ethyl alcohol, propyl alcohol and butyl alcohol are particularly preferred. Ethyl alcohol and butyl alcohol are particularly advantageous.

$R_4$ is preferably a straight or branched $C_1$-$C_{12}$ alkyl group, more preferably a $C_2$ or $C_4$ alkyl group.

By $C_6$-$C_{24}$ dicarboxylic acids, aliphatic diacids are meant, preferably of the alpha-omega type. Suberic acid, azelaic acid, brassilic acid and their mixtures are particularly preferred.

By $C_6$-$C_{24}$ monocarboxylic acids, monoacids are meant, which may have one or more unsaturations along the chain, and which may or may not be substituted.

Preferred unsubstituted monocarboxylic acids are monoacids having a $C_9$-$C_{24}$ chain length; particularly preferred are palmitic, stearic, oleic, arachidic, behenic or lignoceric acids.

Preferred substituted monocarboxylic acids are long chain monocarboxylic acids with one or more ketone groups or hydroxyl groups in a non-terminal position, and among these $C_{12}$-$C_{24}$ carboxylic acids containing at least one ketone group or $C_{12}$-$C_{24}$ hydroxy acids containing at least one secondary hydroxyl group are particularly preferred. Examples of preferred substituted monocarboxylic acids are 9-hydroxystearic acid, 9-ketostearic acid, 10-ketostearic acid and 10-hydroxystearic acid.

Said substituted monocarboxylic acids may contain two adjacent hydroxyl groups or one hydroxyl group adjacent to a ketone group. If two adjacent hydroxyl groups are present, dihydroxypalmitic, dihydroxystearic, dihydroxyoleic, dihydroxyarachidic and dihydroxybehenic acids are preferred; 9,10-dihydroxystearic acid is particularly preferred.

Advantageously, the oligomeric structures prepared according to the invention are dimer or trimer esters of triglycerides in which the number of repeated units (n) is 2 or 3.

Dimer and trimer esters of triglycerides containing $C_6$-$C_{24}$ dicarboxylic acid residues are particularly preferred. Examples of preferred dimer and trimer esters are illustrated by the following structures:

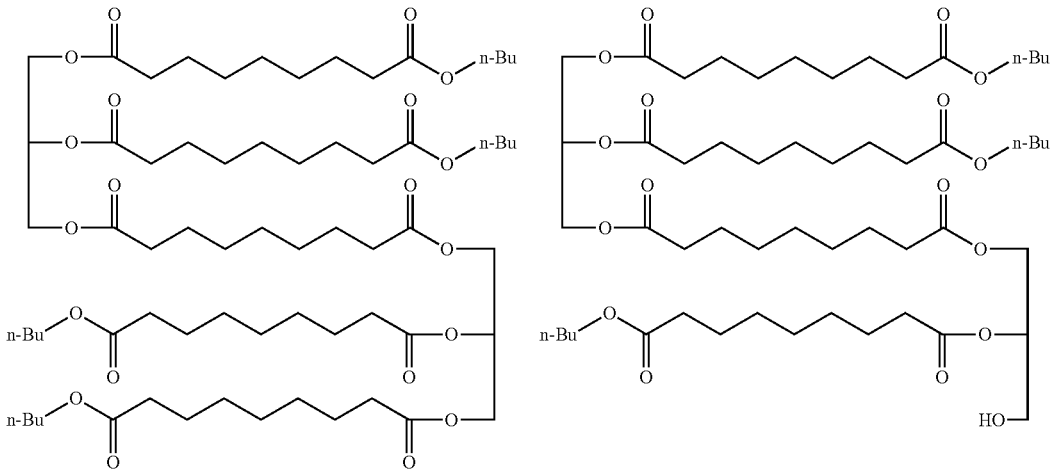

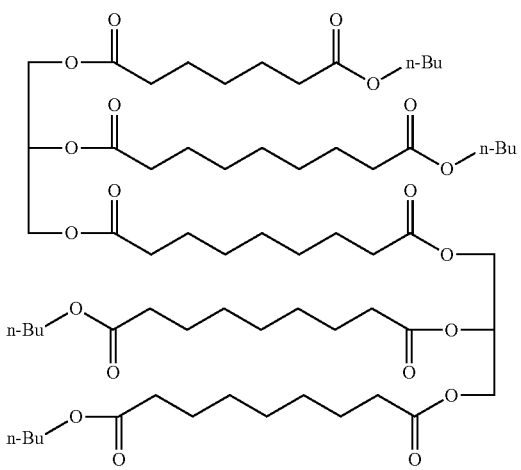

-continued
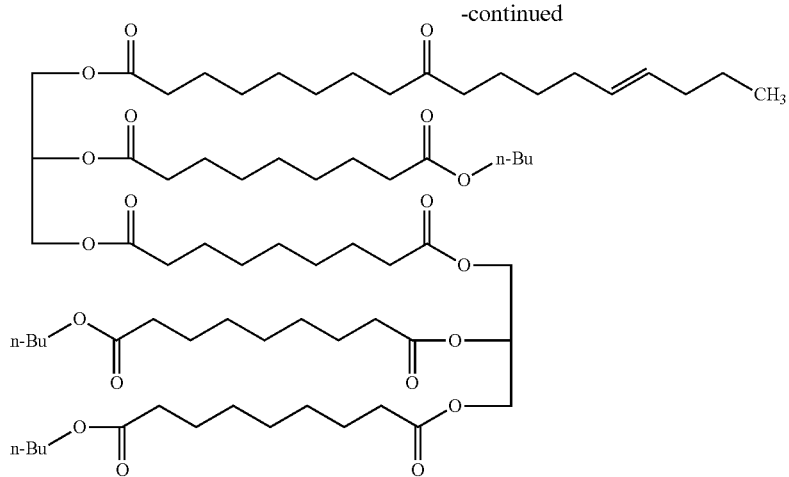
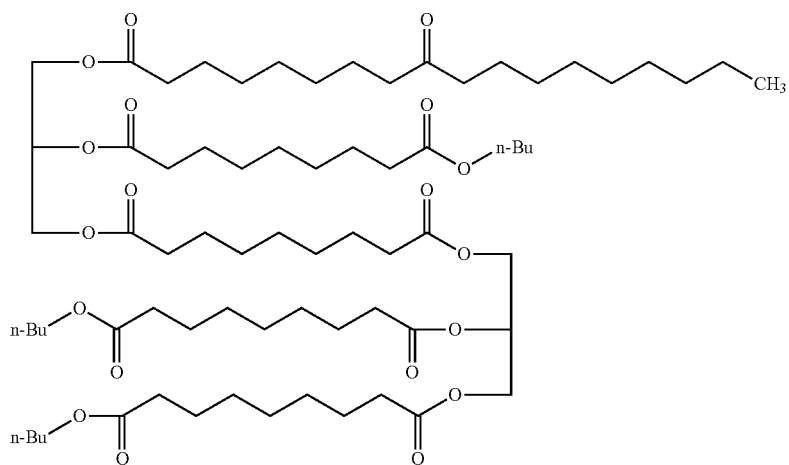
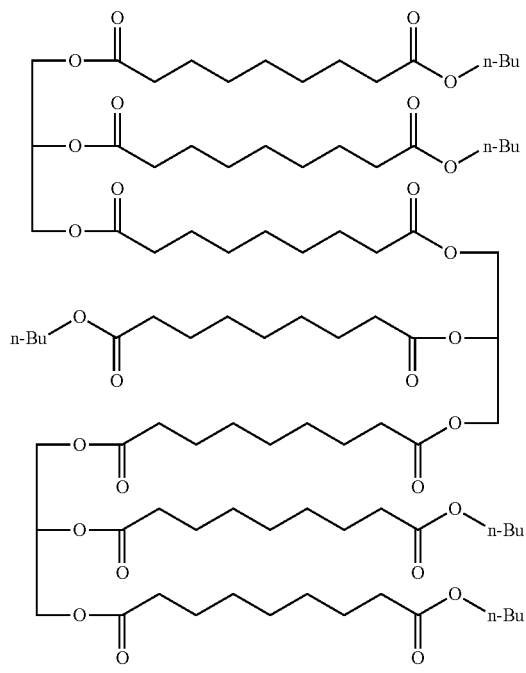

Other examples of oligomeric structures prepared according to the invention have $R_1=C_7$ alkylenes, $R_4=C_4$ alkyls, $n=2$ and $R_2$ and $R_3$ independently selected from the following groups:

—C(O)—(CH$_2$)$_{6-10}$—COOBu
—C(O)—(CH$_2$)$_{16}$—COOBu
—C(O)—(CH$_2$)$_{6-10}$—CH$_3$
—C(O)—(CH$_2$)$_{16}$—CH$_3$
—C(O)—(CH$_2$)$_{8-9}$—(CH$_2$)$_{7-8}$—CH$_3$
—C(O)—(CH$_2$)$_6$—CO—(CH$_2$)$_7$—CH=CH—CH$_3$.

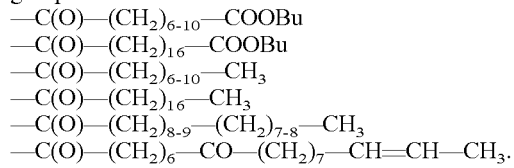

The mixtures of triglycerides prepared according to this invention may contain monomeric triglycerides containing at least one $C_6$-$C_{24}$ dicarboxylic acid residue. Monomeric triglycerides containing two $C_6$-$C_{24}$ dicarboxylic acid residues, the said dicarboxylic acids being the same or different, are particularly preferred. Monomeric triglycerides containing at least one $C_6$-$C_{24}$ dicarboxylic acid residue and at least one $C_6$-$C_{24}$ monocarboxylic acid residue having at least one ketone group and/or at least one hydroxyl group are also preferred. The carboxylic acid residues present in the said monomeric triglycerides are esterified with straight or branched $C_1$-$C_{12}$ monoalcohols.

Preferably the mixtures of triglyceride prepared according to this invention also contain oligoglycerols such as diglycerol and triglycerol and their esters with mono- or dicarboxylic acids. Esters of diglycerol and triglycerol comprising one or more $C_6$-$C_{24}$ dicarboxylic acids are preferred. Diglycerol and triglycerol esters comprising at least one saturated or unsaturated monocarboxylic acid containing one or more hydroxyl groups and/or a ketone group are also preferred.

As far as the alcohols used for the esterification reaction in the process according to this invention are concerned, straight or branched $C_1$-$C_{12}$ aliphatic alcohols are meant. Short chain linear alcohols such as for example methyl alcohol, ethyl alcohol, propyl alcohol and butyl alcohol are particularly preferred. Ethyl alcohol and butyl alcohol are particularly advantageous.

According to one aspect of this invention, the esterification stage according to this invention is performed in the absence of catalysts. In this case the reaction is preferably performed by heating the esterification reactor to temperatures between 50 and 250° C., more preferably between 100 and 220° C., even more preferably between 150 and 210° C. Preferably the reaction is performed by removing the water which is formed in the course of the reaction. The excess alcohol and volatile esters can be separated from the esterification product, preferably by evaporation under vacuum.

According to another aspect of this invention, the esterification stage according to this invention is performed in the presence of an acid catalyst consisting of one or more phosphorus compounds.

By acid catalysts consisting of one or more phosphorus compounds are meant mineral acids containing phosphorus, such as for example oxyacids, their organic derivatives in which the acid is esterified with alcohols, or their mixtures.

Examples of phosphorus oxyacids suitable for catalysing the process according to the invention are phosphoric acid or orthophosphoric acid, phosphonic acid, oligo- or polyphosphoric acids, condensation products of phosphoric acid, or their mixtures. The condensation products of phosphoric acid may be linear (for example pyrophosphoric acid, tripolyphosphoric acid, tetrapolyphosphoric acid), cyclic (such as for example trimetaphosphoric acid) or branched.

The use of orthophosphoric acid is particularly advantageous.

Esters of these mineral acids containing phosphorus, in particular esters or phosphates obtained by condensation with short chain alcohols, are also suitable for catalysing the esterification reactions according to this invention. Mono-, di- or tri-esters having short chain alkyl radicals such as for example the methyl, ethyl, propyl and butyl groups, are preferred among these phosphoric esters or phosphates. Catalysts comprising ethylated or butylated phosphates are particularly preferred.

If the reaction is performed in the presence of an acid catalyst consisting of one or more phosphorus compounds, the reaction is preferably performed by heating the esterification reactor to temperatures between 50 and 200° C., more preferably between 60 and 180° C., and even more preferably between 80 and 140°. Preferably the reaction is performed by removing the water which is formed in the course of the reaction, for example by evaporation under vacuum. The esterification product may be purified to remove the acid catalyst; the excess alcohol and the volatile esters can then be separated, preferably by evaporation under vacuum. The catalyst may be removed for example by washing with water or basic solutions, for example aqueous solutions of sodium bicarbonate. If phosphoric acid is used the catalyst is advantageously removed by washing with distilled water alone.

The presence of oligomeric structures prepared according to the invention may be determined by different analytical methods which are well known to those skilled in the art, such as chromatographic methods combined with mass spectrometry, e.g. LC/MS analyses.

In the process for the preparation of mixtures of triglycerides comprising oligomer structures according to this invention the starting mixture of one or more triglycerides containing saturated dicarboxylic acids is obtained from vegetable oils and may contain free $C_6$-$C_{24}$ monocarboxylic and $C_6$-$C_{24}$ dicarboxylic acids, triglycerides of dicarboxylic and monocarboxylic $C_6$-$C_{24}$ acids, di- and tri-glycerides containing one or more of the following groups consisting of dicarboxylic $C_6$-$C_{24}$ acid residues and monocarboxylic $C_6$-$C_{24}$ acid residues.

A preferred starting mixture of one of more triglycerides containing saturated dicarboxylic acids is characterised by Number Average Molecular Weight (Mn) of between 200 and 1000 Da, determined by GPC analysis following calibration with polystyrene standard.

The density of the said starting mixture, determined by weighing 100 mL of the said mixture at a temperature of 100° C., preferably lies between 0.95 and 1.05 g/cm$^3$.

Preferably the kinematic viscosity of said starting mixture calculated as the ratio between the dynamic viscosity (measured using the HAAKE VT 500 rotational viscosimeter fitted with an MV1 rotor at 100° C.) and density lies between 50 and 1500 cSt.

Said starting mixture preferably has an Acid Number of between 50 and 300 mg KOH/g. By Acid Number is meant the quantity of KOH, expressed in mg, required to neutralise the acidity of 1 g of substance. The determination is performed according to standard ASTM D974-07 in the presence of phenolphthalein.

The degree of unsaturation of the starting mixture, expressed by $I_2$ number and determined by titration according to the Wijs' method preferably lies between 0 and 150 g $I_2$/100 g.

The Saponification Number, understood to be the quantity of KOH, expressed in mg, consumed in the saponification of 1 gram of substance, preferably lies between 100 and 450 mg KOH/g. The residual KOH after reflux saponification for 60 minutes is determined by titration with HCl in the presence of phenolphthalein.

The Hydroxyl Number of the starting mixture, understood to be the quantity of potassium hydroxide equivalent to the acetylable hydroxyls in 1 gram of substance, is preferably between 10 and 100 mg KOH/g. This is determined according to standard ASTM D1957-86.

According to a preferred aspect of this invention the starting mixture of one or more triglycerides containing saturated dicarboxylic acid is the product of the oxidative cleavage of vegetable oils performed in batch or continuous mode. One example is the mixture of triglycerides obtained according to the processes described in patent applications WO 2008/138892 and WO 2011/080296. The mixtures of glycerides obtained from the oxidation of sunflower oil and in particular from sunflower oil having a high oleic acid content (HOSO, High Oleic Sunflower Oil) are of particular interest.

According to a particularly preferred aspect of the invention the starting mixture of one or more triglycerides containing saturated dicarboxylic acids is prepared from the organic phase obtained at the end of stage d) (i.e. hydrolysis reaction) of the continuous oxidative cleavage process described in patent application WO 2011/080296. Said organic phase is advantageously evaporated in a thin film evaporator operating at low pressure, preferably at a pressure below 2 kPa, more preferably at a pressure below 1 kPa, with a heat transfer oil temperature between 180-300° C., preferably between 200-290° C., more preferably between 240-280° C., to separate out the free carboxylic acids from the reaction residue. Preferably the feed temperature is between 80 and 120° C., more preferably between 100 and 110° C. The temperature of the vapour phase is preferably between 180 and 220° C., more preferably between 200 and 210°. The temperature of the reaction residue is preferably between 210 and 250° C.

In this case the esterification reaction according to this invention is subsequently performed preferably by using phosphoric acid as catalyst at a temperature of 70-180° C.

The mixtures of triglycerides comprising oligomer structures prepared according to the invention preferably have a kinematic viscosity of between 5 and 400 cSt at 100° C., determined as described above.

The glass transition temperature (Tg) of the mixtures of triglycerides prepared according to the invention is preferably between –85° C. and –40° C., more preferably between –80° C. and –45° C. and even more preferably between –70° C. and –50° C. These Tg values render the mixtures which can be derived from vegetable oils prepared according to the invention particularly suitable for use in elastomeric compositions as a replacement for conventional oils. In particular, it has surprisingly been found that the Tg value of the mixtures prepared according to the invention in the absence of catalyst or using acid catalysts comprising phosphorus compounds is higher than that of mixtures prepared using sulfuric acid as catalyst and close to that of conventional extender oils. This makes the replacement even easier, in that the resulting elastomeric compositions have similar dynamic properties.

Glass transition temperature (Tg) is determined by Differential Scanning Calorimetry in a single run from –100° C. to 30° C. with a rate of temperature change of 20° C./min.

The mixtures of triglycerides comprising oligomeric structures prepared according to this invention preferably have a density of between 0.90 and 1.05 g/cm$^3$ (T=100° C.).

Advantageously the Acid Number of the product is below 50, preferably below 10 and more preferably below 5 mg KOH/g.

According to a preferred aspect the mixtures of triglyceride comprising the oligomeric structures have an $I_2$ Number of between 0 and 140 g $I_2$/100 g.

The Saponification Number of the mixtures of triglycerides comprising oligomeric structures is preferably between 150 and 500 mg KOH/g.

The Hydroxyl Number of the mixtures of triglycerides preferably remains between 10 and 100 mg KOH/g.

The mixtures of triglycerides prepared according to the present invention are insoluble in boiling water. Said mixtures are however completely soluble in diethylether, ethyl alcohol, acetone and chloroform at ambient temperature. They are also characterised by high stability to hydrolysis.

The mixtures of triglycerides prepared according to this invention can be used as extender oils in elastomeric compositions.

They are also characterised by very high stability to hydrolysis and a low pour point. They therefore can be used as special lubricants. Thanks to the high stability to hydrolysis and a low pour point they can also be used as additives for rubbers, in particular as plasticisers. A further possible use of the mixtures of triglycerides according to this invention is as base for inks.

In a particularly preferred embodiment, the mixtures of triglycerides comprising complex oligomeric structures prepared according to this invention may be used as extender oils for elastomeric compositions based on natural rubbers (NR), synthetic rubbers or their mixtures. Examples of synthetic rubbers are diene-based rubbers such as vinylarene-conjugated diene copolymers (e.g. SBR, Styrene-Butadiene Rubber), diene polymers (e.g. polybutadiene, polyisoprene), ethylene-propylene copolymers, in particular ethylene/propylene/diene terpolymers (EPDM, Ethylene/Propylene/Diene Monomer), and thermoplastic elastomers such as styrene-butadiene-styrene (SBS) block copolymers, polar nitrile rubbers, acrylonitrile-butadiene (NBR) copolymers and styrene-isoprene-styrene (SIS) rubbers. The use of elastomeric compositions based on natural rubbers or styrene-butadiene rubbers is particularly advantageous.

If used as an extender oil the mixtures of triglycerides comprising oligomeric structures prepared according to the invention are used as such or in a mixture with mineral and/or natural oils. Examples of mineral oils are DAE, TDAE and MES; examples of natural oils are oils of animal and plant origin including: peanut oil, *Brassicaceae* oils, hemp oils, safflower oils, coconut oils, sunflower oils with a various oleic content, jatropha oils, linseed oils, olive oils, macadamia oils, mahua oils, neem oils, palm oils, poppy oils, pongamia oils, castor oils, rice oils, rubber tree seed oils (*Hevea brasiliensis*), maize seed oils, mustard oils, sesame oils and grape seed oils.

The resulting elastomeric compositions may also contain vulcanisers (e.g. sulphur) and vulcanisation accelerators, activators and retardants, organic acids, antioxidants, fillers, process coadjuvants and other additives, as known in the art.

These elastomeric compositions containing complex oligomeric structures which can be derived from vegetable oils according to the present invention are used in particular in the production of tyres.

The process for the preparation of mixtures of triglycerides comprising oligomeric structures according to the invention will now be described using non-limiting examples.

EXAMPLES

Preparation of the Starting Mixture

The starting mixture of triglycerides containing dicarboxylic acids was obtained from the organic phase after stage d) of hydrolysis at the end of the process of oxidative cleavage of sunflower oil described in patent application WO 2011/080296. The free carboxylic acids present in the organic phase were evaporated in a thin film evaporator operating at a pressure of 500 Pa, with heat transfer oil at a temperature of 270° C. under the following operating conditions:

Feed temperature=105° C.
Vapour phase temperature=205° C.
Reaction residue temperature=250° C.
The Mn for the mixture was 215 Da.

This mixture of triglycerides containing saturated dicarboxylic acids was esterified with butyl alcohol in the following examples.

Characterisation of the Product

Molecular Weights were determined by Gel Permeation Chromatography (GPC), using an Agilent 1100 liquid chromatograph equipped with three 5-μm PL gel columns connected in series with porosities $10^4$, $10^3$ and 500 Angstrom (Å). Chloroform at a flow rate of 1 mL/min was used as eluent. The calibration curve was constructed using polystyrene standards. The column temperature was set at 40° C. The samples were dissolved in chloroform (0.15 mg/ml) filtered through teflon filters (pore diameter: 0.20 μm).

Corrosion Test

The corrosion test was performed repeating the esterification reaction described in the examples five times using a metal test piece as the blade of the mechanical stirrer.

Metal test pieces of rectangular shape (approximately 50 mm×20 mm with a thickness of approximately 3 mm) of 316 L stainless steel were used to carry out the corrosion test. Before starting each test the weight of each test piece was determined using an analytical balance (arithmetic mean of three successive weighing sessions) and its surface area in contact with the reaction medium was determined.

The surface area in contact with the reaction medium [mm$^2$] was calculated by measuring the precise dimensions of the test piece (length, width and thickness) using a caliper gauge and applying the following formula:

Surface area in contact with the reaction medium $[mm^2]=2\cdot(b\cdot c+b\cdot d+c\cdot d)-e$ in which
b=length
c=width
d=thickness
e=surface area of the test piece occupied by the connection to the mechanical stirrer (and therefore not in contact with the reaction medium).

After each reaction the test piece was removed from the mechanical stirrer and washed under the conditions described in NACE Standard TM0169-2000 for stainless steel test pieces (10% w/w $HNO_3$ at 60° C. up to complete removal of any material adhering to it) and then with distilled water at ambient temperature. The test piece was then dried in a ventilated stove at 60° C.

Once returned to ambient temperature the test piece was weighed on an analytical balance and the weight was calculated as the arithmetic mean of three successive weighing sessions.

After recording the weight the test piece was again fitted on the mechanical stirrer to carry out the next esterification reaction.

The corrosion rate was determined using the following formula

Corrosion rate [mm/year]=$(\Delta p)\cdot 365/(A\times d\times t)$ in which
$\Delta p$ [mg]=loss of weight from the metal test piece
A [mm$^2$]=surface area of the metal test piece in contact with the reaction medium at the start of the test
d [g/cm$^3$]=density of the material of which the metal test piece was made (density of 316 L stainless steel=7.98 g/cm$^3$)
t [days]=total duration of the test (=sum of the five reaction times)

Comparative Example

The starting mixture (mixture of triglycerides containing dicarboxylic acids) prepared as described above was esterified with butyl alcohol using sulfuric acid as catalyst. The reaction was performed in a 500 ml glass flask fitted with a mechanical agitator in which the paddle was replaced by a 316 L stainless steel test piece in order to carry out the corrosion test (test piece dimensions=40.8×14.7×3.0 mm). The reaction mixture was heated under reflux at 104° C. for 8 hours removing the water formed in the course of the reaction through distillation.

The reaction product was then purified by washing with distilled water and an aqueous solution of sodium bicarbonate to remove the acid catalyst; the excess volatile butyl alcohol and butyl esters were then separated off by evaporation under vacuum (pressure=10 Pa, temperature of the vapours from 80-190° C.).

The Mn for the mixtures of triglycerides containing oligomeric structures prepared by the esterification reaction according to the invention was 1950 Da.

The esterification reaction was repeated another four times in order to carry out the corrosion test. After the test the corrosion rate was found to be over 0.50 mm/year.

Example 1

Esterification with Phosphoric Acid and Butanol

The starting mixture used in the previous example was esterified with butyl alcohol according to the invention using a phosphoric acid catalyst. The reaction was carried out in a 500 mL glass flask fitted with a mechanical stirrer in which the paddle had been replaced by a 316 L stainless steel test piece in order to carry out the corrosion test (test piece dimensions=51.3×19.5×2.9 mm). The reaction mixture was heated to a temperature of 130° C. under reflux for 8 hours, the water forming in the course of the reaction being removed by distillation.

The acid catalyst was removed by a plain washing with distilled water.

The excess of volatile butyl alcohol and butyl esters was then separated off by evaporation under vacuum under the same conditions as in the previous example (pressure=10 Pa; temperature of the vapours from 80-190° C.).

The Mn of the mixtures of triglycerides containing oligomer structures prepared using the esterification reaction according to the invention was 1665 Da.

The esterification reaction was repeated another four times in order to carry out the corrosion test. At the end of the test the corrosion rate was 0.07 mm/year.

For equal catalytic activity the use of orthophosphoric acid appreciably reduces the corrosion rate of the reaction equipment.

The invention claimed is:

1. Process for the preparation of mixtures of triglyceride comprising one or more of the following oligomeric structures:

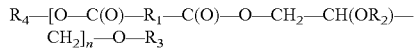

wherein
R$_1$ is selected from C$_2$-C$_{22}$ alkylenes,
R$_2$ is selected from one or more of the following groups consisting of C$_6$-C$_{24}$ dicarboxylic acid residues and C$_6$-C$_{24}$ monocarboxylic acid residues,
R$_3$ is selected from one or more of the following groups consisting of H, C$_6$-C$_{24}$ dicarboxylic acid residues and C$_6$-C$_{24}$ monocarboxylic acid residues,
R$_4$ is an alkyl group,
n is an integer equal to or greater than 2,
said C$_6$-C$_{24}$ dicarboxylic acids of R$_2$ and R$_3$ being esterified with monoalcohols and said mixture of triglycerides having a Number Average Molecular Weight (Mn) of between 800 and 10,000 Da,
which comprises the step of esterification of a mixture of one or more triglycerides containing saturated dicarboxylic acids with alcohols at temperatures between 50 and 250° C. and which occurs in the absence of catalyst or in the presence of an acid catalyst consisting of one or more phosphorus compounds.

2. Process according to claim 1, wherein said esterification step occurs at temperatures between 60 and 180° C. and in presence of an acid catalyst consisting of one or more phosphorus compounds.

3. Process according to claim 2, wherein said esterification step occurs at temperatures between 80 and 140° C. and in the presence of an acid catalyst consisting of one or more phosphorus compounds.

4. Process according to claim 1, wherein the acid catalyst consisting of one or more phosphorus compounds is selected from: phosphorus containing mineral acids, their organic derivatives wherein the acid is esterified with alcohols or their mixtures.

5. Process according to claim 4, wherein said acid catalyst consisting of one or more phosphorus compounds is selected from: phosphoric acid, phosphonic acid, oligo- or polyphosphoric acids, phosphoric acid condensation products or phosphoric acid esters, or their mixtures.

6. Process according to claim 5 wherein the said acid catalyst comprises phosphoric acid.

7. Process according to claim 1, wherein said esterification step occurs at temperatures between 100 and 220° C. and in absence of catalyst.

8. Process according to claim 7, wherein said esterification step occurs at temperatures between 150 and 210° C. in the absence of catalyst.

9. Process according to claim 1, wherein said esterification step is performed by removing the water which is formed in the course of the reaction.

10. Process according to claim 1, wherein the mixture of one or more triglycerides containing saturated dicarboxylic acids is the product of the oxidative cleavage of vegetable oils.

11. Process according to claim 2, wherein the acid catalyst consisting of one or more phosphorus compounds is selected from: phosphorus containing mineral acids, their organic derivatives wherein the acid is esterified with alcohols or their mixtures.

12. Process according to claim 3, wherein the acid catalyst consisting of one or more phosphorus compounds is selected from: phosphorus containing mineral acids, their organic derivatives wherein the acid is esterified with alcohols or their mixtures.

13. Process according to claim 2, wherein said esterification step is performed by removing the water which is formed in the course of the reaction.

14. Process according to claim 3, wherein said esterification step is performed by removing the water which is formed in the course of the reaction.

15. Process according to claim 4, wherein said esterification step is performed by removing the water which is formed in the course of the reaction.

16. Process according to claim 5, wherein said esterification step is performed by removing the water which is formed in the course of the reaction.

17. Process according to claim 6, wherein said esterification step is performed by removing the water which is formed in the course of the reaction.

18. Process according to claim 7, wherein said esterification step is performed by removing the water which is formed in the course of the reaction.

19. Process according to claim 8, wherein said esterification step is performed by removing the water which is formed in the course of the reaction.

20. Process according to claim 2, wherein the mixture of one or more triglycerides containing saturated dicarboxylic acids is the product of the oxidative cleavage of vegetable oils.

* * * * *